US00PP17107P2

(12) United States Plant Patent
Schreurs

(10) Patent No.: US PP17,107 P2
(45) Date of Patent: Sep. 19, 2006

(54) HYBRID TEA ROSE PLANT NAMED 'SCHRETROJE'

(50) Latin Name: *Rosa hybrida*
Varietal Denomination: Schretroje

(75) Inventor: Petrus Nicolaas Johannes Schreurs, De Kwakel (NL)

(73) Assignee: Schreurs Holding B.V., De Kwakel (NL)

( * ) Notice: Subject to any disclaimer, the term of this patent is extended or adjusted under 35 U.S.C. 154(b) by 136 days.

(21) Appl. No.: 10/109,951

(22) Filed: Mar. 29, 2002

(51) Int. Cl.
*A01H 5/00* (2006.01)

(52) U.S. Cl. ..... Plt./134

(58) Field of Classification Search ..... Plt./134, Plt./104, 145
See application file for complete search history.

(56) References Cited

PUBLICATIONS

UPOV–ROM, 2003/02, Plant Variety Database, GTI Jouve Retrival Software, 2 citations for 'Schretroje', 2003.*
Copy of PBR Certificate 01528, 2002.07.05.*

* cited by examiner

*Primary Examiner*—Howard J. Locker
(74) *Attorney, Agent, or Firm*—C. A. Whealy

(57) ABSTRACT

A new and distinct Hybrid Tea Rose plant named 'Schretroje', characterized by its glossy dark green leaves; freely branching habit; yellow-colored flowers; and good postproduction longevity.

1 Drawing Sheet

Botanical classification/cultivar designation: *Rosa hybrida* cultivar Schretroje.

BACKGROUND OF THE INVENTION

The present invention relates to a new and distinct cultivar of Hybrid Tea Rose plant, botanically known as *Rosa hybrida,* commercially produced as a cut flower, and hereinafter referred to by the name 'Schretroje'.

The new cultivar is a product of a planned breeding program conducted by the Inventor in De Kwakel, The Netherlands. The objective of the breeding program was to develop new spray-type cut Rose cultivars with attractive flower petal colors, long and strong stems, and good postproduction longevity.

The new cultivar originated from a cross-pollination made by the Inventor in 1997 of two unnamed proprietary selections, not patented. The cultivar Schretroje was discovered and selected by the Inventor as a flowering plant within the progeny of the stated cross-pollination in a controlled environment in De Kwakel, The Netherlands.

Since 1998, asexual reproduction of the new cultivar by cuttings in De Kwakel, The Netherlands has shown that the unique features of the new cultivar are stable and reproduced true to type in successive generations of asexual reproduction.

SUMMARY OF THE INVENTION

The following traits have been repeatedly observed and are determined to be the unique characteristics of 'Schretroje'. These characteristics in combination distinguish the new Hybrid Tea Rose as a new and distinct cultivar:

1. Glossy dark green leaves.
2. Freely branching habit.
3. Yellow-colored flowers.
4. Good postproduction longevity.

Plants of the Hybrid Tea Rose differ primarily from plants of the parent selections in flower color.

Plants of the Hybrid Tea Rose can be compared to plants of the cultivar Schrakirk, not patented. In side-by-side comparisons conducted in De Kwakel, The Netherlands, plants of the new cultivar differed from plants of the cultivar Schrakirk in the following characteristics:

1. Plants of the new Hybrid Tea Rose had more thorns per lateral branch than plants of the cultivar Schrakirk.
2. Plants of the new Hybrid Tea Rose had larger and more leaves per lateral branch than plants of the cultivar Schrakirk.
3. Plants of the new Hybrid Tea Rose were not as freely flowering as plants of the cultivar Schrakirk.
4. Flowers of plants of the new Hybrid Tea Rose had larger flowers with more petals per flower than flowers of plants of the cultivar Schrakirk.
5. Flower color of plants of the new Hybrid Tea Rose was lighter yellow than flower color of plants of the cultivar Schrakirk.

Plants of the new Hybrid Tea Rose have not been observed under all possible environmental conditions. The phenotype may vary significantly with variations in environment such as temperature and light intensity without, however, any variance in genotype.

BRIEF DESCRIPTION OF PHOTOGRAPH

The accompanying colored photograph illustrates the new Hybrid Tea Rose plant, showing the colors as true as it is reasonably possible to obtain in colored reproductions of this type. Colors in the photograph may differ slightly from the color values cited in the detailed botanical description which accurately describe the colors of the new Hybrid Tea Rose.

The photograph comprises a top perspective view of a typical flowering stem of the new Hybrid Tea Rose.

DETAILED BOTANICAL DESCRIPTION

The aforementioned photograph and following observations and measurements describe cut flowering stems of plants grown in De Kwakel, The Netherlands, in a glass-covered greenhouse with day and night temperatures about 19 and 15° C., respectively. Flowering stems used in the photograph and the description were about five months old and had been pruned. In the following description, color references are made to The Royal Horticultural Society Colour Chart, 1995 Edition, except where general terms of ordinary dictionary significance are used.

Botanical classification: *Rosa hybrida* cultivar Schretroje.

Commercial classification: Hybrid Tea Rose used as a cut flower.

Parentage:

*Female, or seed, parent.*—Unidentified *Rosa hybrida* proprietary selection, not patented.

*Male, or pollen, parent.*—Unidentified *Rosa hybrida* proprietary selection, not patented.

Propagation:

*Type.*—By cuttings grafted onto rootstocks. Typically the *Rosa canina* cultivar Inermis, not patented, is used as the rootstock.

Plant description:

*Form/growth habit.*—Upright and somewhat outwardly spreading; vigorous.

*Productivity.*—In The Netherlands and at a planting density of seven plants per square meter, productivity is about 180 to 200 flowering stems per square meter per year.

*Plant height.*—About 82.5 cm.

*Plant diameter or spread.*—About 97.5 cm.

*Lateral branches* (*flowering stems*).—Quantity per pruned plant: Freely branching, about eight. Lateral branch length: About 82.5 cm; stems initially grow outwardly before becoming erect. Lateral branch diameter: About 5.5 mm. Internode length: About 5 cm. Texture: Smooth; glabrous. Strength: Strong. Aspect: Erect. Color: 137B. Thorns: Quantity per 4 centimeters of stem: About seven. Length: About 7.5 mm. Width at base: About 7.5 mm. Shape: Roughly deltoid. Apex: Acute. Base: Flat. Margin: Entire. Color: Towards apex, 179C; towards base, 147C.

*Foliage description.*—Arrangement: Alternate; compound with about three, five or seven leaflets per leaf. Quantity of leaves per lateral branch: About 18. Leaf length (seven-leaflet leaf): About 16 to 20 cm. Leaf width (seven-leaflet leaf): About 13 to 16 cm. Terminal leaflet length: About 9 cm. Terminal leaflet width: About 5.5 cm. Lateral leaflet length: About 6.5 cm. Terminal leaflet width: About 3.75 cm. Leaflet shape: Ovate. Leaflet apex: Acuminate. Leaflet base: Obtuse. Leaflet margin: Serrulate. Leaflet texture, upper and lower surfaces: Smooth, leathery, glabrous. Leaflet venation pattern: Pinnate. Leaf petiole length: About 4 cm. Leaf petiole diameter: About 2 mm. Leaflet petiole length: About 5.5 cm. Leaflet petiole diameter: About 1 mm. Stipules: Quantity: Two at base of petiole. Length: About 2.3 cm. Width: About 1 cm. Texture, upper and lower surfaces: Smooth, leathery, glabrous. Color: Young foliage, upper surface: 137A. Young foliage, lower surface: 191A. Fully expanded foliage, upper surface: 147A. Fully expanded foliage, lower surface: 191A. Venation, upper surface: 146A to 146B. Venation, lower surface: 148C. Leaf and leaflet petiole, upper and lower surfaces: 144A. Stipules, upper surface: 137C. Stipules, lower surface: 144A.

Flower description:

*Flower type and habit.*—Consistently symmetrical double flowers; petals arranged in rosettes. Flowers arranged singly at terminals. Petals not persistent; receptacles persistent.

*Flowering season/time to flower.*—Year-round under greenhouse conditions.

*Flower diameter, fully opened.*—About 11 cm.

*Flower depth* (*height*), *fully opened.*—About 4.25 cm.

*Flower longevity as a cut flower.*—About two weeks.

*Flower longevity on the plant.*—About three weeks.

*Fragrance.*—None detected.

*Flower buds.*—Shape: Ovoid. Length: About 3.5 cm. Diameter: About 2.5 cm. Color (underside of petals): 8C.

*Petals.*—Quantity per flower: About 54. Length: About 3.5 to 5 cm. Width: About 3.2 to 7 cm. Shape: Obovate. Apex: Rounded. Margin: Entire. Texture, upper and lower surfaces: Smooth, glabrous, satiny. Aspect: Initially upright and reflexing with development. Color: When opening, upper surface: 12A. When opening, lower surface: 8B. Fully opened, upper surface: 5B; becoming closer to 1C with subsequent development. Fully opened, lower surface: 1C.

*Sepals.*—Quantity per flower: About five. Length: About 4.5 cm. Width: About 7 mm. Shape: Lanceolate. Apex: Apiculate. Base: Cuneate; fused at receptacle. Margin: Ciliate. Texture, upper and lower surfaces: Satiny; pubescent. Color, upper surface: 138B. Color, lower surface: 146B.

*Reproductive organs.*—Stamens: Quantity per flower: About 170. Anther length: About 3 mm. Anther diameter: About 1 mm. Anther shape: Elliptic. Anther color: 20A. Filament color: 21B. Pollen: None observed. Pistils: Quantity per flower: About 100. Pistil length: About 3 mm. Style length: About 2 mm. Style color: 4D. Stigma shape: Bi-lobed. Stigma color: 2B. Receptacle height: About 2.2 cm. Receptacle diameter: About 1.5 cm. Receptacle color: 144A.

*Seed/fruit.*—None observed.

Disease/pest resistance: Plants of the new Hybrid Tea Rose have not been observed to be resistant to pathogens and pests common to *Rosa*.

It is claimed:

1. A new and distinct Hybrid Tea Rose plant named 'Schretroje', as illustrated and described.

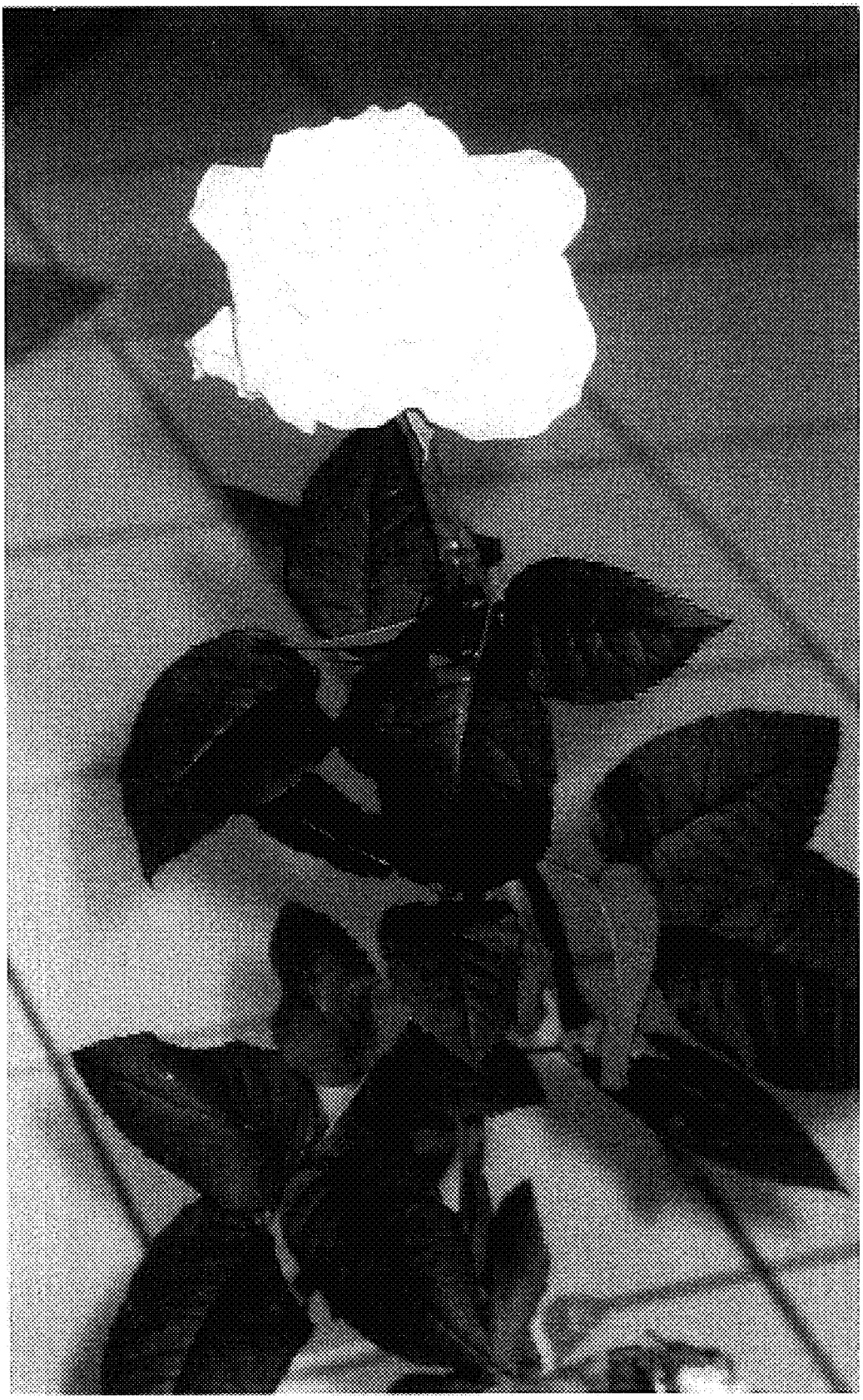

* * * * *